(12) United States Patent
Singh et al.

(10) Patent No.: US 6,696,426 B2
(45) Date of Patent: Feb. 24, 2004

(54) PRESERVATIVE FREE OPHTHALMIC OXAZOLIDINONE ANTIBIOTIC DRUG DELIVERY SYSTEMS

(75) Inventors: Satish K. Singh, Portage, MI (US); Lisa A. Adams, Mattawan, MI (US); Paramita Bandyopadhyay, Portage, MI (US); Syed Hasan, Portage, MI (US); Leslie C. Hawley, Kalamazoo, MI (US); Sandra M. Sims, Portage, MI (US)

(73) Assignee: Pharmacia Corporation, Peapack, NJ (US)

( * ) Notice: Subject to any disclaimer, the term of this patent is extended or adjusted under 35 U.S.C. 154(b) by 0 days.

(21) Appl. No.: 10/080,810

(22) Filed: Feb. 22, 2002

(65) Prior Publication Data

US 2003/0027790 A1 Feb. 6, 2003

Related U.S. Application Data

(63) Continuation-in-part of application No. 09/933,366, filed on Aug. 20, 2001, which is a continuation-in-part of application No. 09/974,598, filed on Oct. 10, 2001, now Pat. No. 6,551,584.
(60) Provisional application No. 60/285,347, filed on Apr. 20, 2001, provisional application No. 60/226,846, filed on Aug. 22, 2000, and provisional application No. 60/239,136, filed on Oct. 10, 2000.

(51) Int. Cl.$^7$ ..................... A61K 31/715; A61K 31/535
(52) U.S. Cl. ..................... 514/58; 514/235.8; 424/427
(58) Field of Search ............................. 514/235.8, 912, 514/58; 424/427

(56) References Cited

U.S. PATENT DOCUMENTS

| | | | |
|---|---|---|---|
| 5,538,721 A | 7/1996 | Babcock et al. | 424/78.04 |
| 5,646,294 A | 7/1997 | Bartroli et al. | 548/267.2 |
| 2002/0068720 A1 | 6/2002 | Sims | 514/58 |
| 2002/0156072 A1 * | 10/2002 | Barbachyn et al. | 514/227.8 |

OTHER PUBLICATIONS

Arima et al., (2001), Comparative Studies of the Enhancing Effects of Cyclodextrins on the Solubility and Oral Bioavailability of Tacrolimus in Rats, *Journal of Pharmaceutical Sciences*, vol. 90, No. 6, pp. 690–701.
Conners, (1997), The Stability of Cyclodextrin Complexes in Solution, *Chem. Rev.* 97, pp. 1325–1357.
Faucci et al., (2002), Computer–aided molecular modeling techniques for predicting the stability of drug–cyclodextrin inclusion complexes in aqueous solutions, 358, pp. 383–390.
Lipkowitz, (1998), Applications of Computational Chemistry to the Study of Cyclodextrins, *Chem. Rev.*, 98, ppo. 1829–1873.
Lotsson et al., (1989), Effects of 2–hydroxpropyl–β–cyclodextrin on the aqueous solubility of drugs and transdermal delivery of 17β–estradiol, *Acta Pharm. Nord.*, 1(4), pp. 185–194.
Loftsson et al., (1991), Solubilization and stabilization of drugs through cyclodextrin complexation, *Act Pharm. Nord.*, 3(4), pp. 215–217.
Loftsson et al., (1994), 2–Hydroxypropyl–β–cylodextrin in topical carbonic anhydrase inhibitor formulations, *European Journal of Pharmaceutical Science*, 1, pp. 175–180.
Loftsson et al., (1996), Pharmaceutical Applications of Cyclodextrins. 1. Drug Soulubilization and Stabilization, *Journal of Pharmaceutical Sciences*, vol. 85, No. 10, pp. 1017–1025.
Pagington, (1987), β–Cyclodextrin: the success of molecular inclusion, *Chemistry in Britain*, pp. 455–458.
Pitha et al., (1983), Molecular Encapsulation of Drugs By Cyclodextrins And Congeners, *Controlled Drug Delivery*, vol. 1, pp. 125–148.
Pitha et al., (1986), Hydroxypropyl–β–cyclodextrin: preparation and characterization; effects on solubility of drugs, *International Journal of Phamaceutics*, 29, pp. 73–82.
Schneider et al., (1998), NMR Studies of Cyclodextrins and Cyclodextrin Complexes, *Chem. Rev.*, 98, pp. 1755–1785.
Stella, (1997), Cyclodextrins: Their Future in Drug Formulation and Delivery, *Pharmaceutical Research*, vol. 14, No. 5., pp. 556–567.
Szejtli, (1998), Introduction and General Overview of Cyclodextrin Chemistry, *Chem. Rev.*, 98, pp. 1743–1753.
Uekama, (1987), Cyclodextrin Inclusion Compounds: Effects on Stability and Bio–Pharmaceutical Properties, *Topics in Pharmaceutical Sciences*, pp. 181–194.
Uekama, et al., (1987), Cyclodextrins in Drug Carrier Systems, *Critical Reviews in Therapeutic Drug Carrier Systems*, 3(1), pp. 1–40.
Uekama, et al., (1998), Cyclodextrin Drug Carrier System, *Chem. Rev.*, 98, pp. 2045–2076.

* cited by examiner

*Primary Examiner*—James H. Reamer
(74) *Attorney, Agent, or Firm*—Karen B. King; Charles W. Ashbrook

(57) ABSTRACT

There is provided a pharmaceutical preservative free composition suitable for topical administration to an eye, the composition comprising (a) an oxazolidinone antimicrobial drug, for example linezolid, in a therapeutically or prophylactically effective drug concentration that is above the practical limit of solubility of the drug in a substantially isotonic aqueous solution at a physiologically compatible pH, and (b) a pharmaceutically acceptable cyclodextrin compound in a concentration sufficient to maintain the drug in solution at such a drug concentration. The composition is particularly useful for the treatment and/or prevention of eye infections due to gram positive bacteria.

25 Claims, 1 Drawing Sheet

PRESERVATIVE FREE OPHTHALMIC OXAZOLIDINONE ANTIBIOTIC DRUG DELIVERY SYSTEMS

This application is a continuation-in-part of U.S. Pat. Ser. No. 09/933,366 filed Aug. 20, 2001, claiming the benefit of U.S. Provisional Application No. 60/285,347, filed Apr. 20, 2001 and of U.S. Provisional Application No. 60/226,846, filed Aug. 22, 2000. This application is also a continuation-in-part of U.S. Pat. Ser. No. 09/974,598, filed Oct. 10, 2001 now U.S. Pat. No. 6,551,584, claiming the benefit of U.S. Provisional Application No. 60/239,136, filed Oct. 10, 2000.

FIELD OF THE INVENTION

The present invention relates to a pharmaceutical composition in an aqueous solution form useful for administration to an eye of a subject for treatment or prevention of infectious disease therein. In particular, the present invention relates to such a composition having as an active agent an oxazolidinone antibiotic drug. The field of the present invention also includes therapeutic or prophylactic use of such a composition, and use of such a composition in preparation of a medicament.

BACKGROUND OF THE INVENTION

Numerous oxazolidinone compounds have been reported as having therapeutically and/or prophylactically useful antibiotic or antimicrobial, in particular an antibacterial, effect. Among such compounds are those illustratively disclosed in the following patents, each of which is individually incorporated herein by reference.

U.S. Pat. No. 5,164,510 to Brickner.
U.S. Pat. No. 5,231,188 to Brickner.
U.S. Pat. No. 5,565,571 to Barbachyn & Brickner.
U.S. Pat. No. 5,627,181 to Riedl et al.
U.S. Pat. No. 5,652,238 to Barbachyn et al.
U.S. Pat. No. 5,688,792 to Barbachyn et al.
U.S. Pat. No. 5,698,574 to Riedl et al.
U.S. Pat. No. 6,069,145 to Betts.

Compounds disclosed in above-cited U.S. Pat. No. 5,688,792 include for example the compound (S)-N-[[3-[3-fluoro-4-(4-morpholinyl)phenyl]-2-oxo-5-oxazolidinyl]methyl]acetamide, referred to herein as "linezolid." Linezolid has the structure shown in formula (I):

(I)

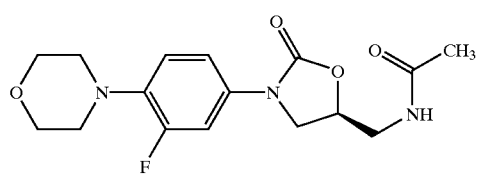

and is in commercial use as a medicament under the trademark Zyvox® of Pharmacia Corporation. Linezolid exhibits strong antibacterial activity against gram-positive organisms including those of the following genera: Staphylococcus (e.g., *Staphylococcus aureus, Staphylococcus epidermidis*), Streptococcus (e.g., *Streptococcus viridans, Streptococcus pneumoniae*), Enterococcus (e.g., *Enterococcus fecalis, Enterococcus faecium*), Bacillus, Corynebacterium, Chlamydia and Neisseria.

Many such gram-positive organisms have developed significant levels of resistance to other antibiotics. Oxazolidinone antibiotics are also generally effective against anaerobic organisms such as those of the genera Bacteroides and Clostridia, and against acid-fast organisms such as those of the genus Mycobacterium.

Above-cited U.S. Pat. No. 5,688,792 discloses that antibiotic oxazolidinone compounds, including linezolid, can be formulated as a gel or cream for topical application to skin.

Many oxazolidinone compounds useful as antibiotics do not form, or do not readily form, salts. For these compounds, and where for any reason it is preferred not to provide the antibiotic in salt form, it is generally difficult to formulate the antibiotic as a solution in a pharmaceutically acceptable liquid carrier, particularly an aqueous carrier. Most such compounds have relatively low solubility in water. In the case of linezolid, for example, the solubility at ambient temperature is less than 3 mg/ml and the practical limit of concentration in aqueous solution is about 2 mg/ml.

Where ophthalmic administration of an oxazolidinone antibiotic drug is contemplated, it is desired to achieve sufficiently high concentrations of the drug to be therapeutically effective in treating eye infections while ensuring all or substantially all of the drug is in solution. Undissolved, particulate, forms of any ingredient of an ophthalmic solution can cause irritation upon administration to the eye of a subject. Some have approached the problem of a need to administer drugs with low solubility to an eye by providing sufficiently dilute aqueous ophthalmic solutions of a poorly soluble drug to ensure that the drug is in solution. Such dilute solutions of drug must be administered to an eye more frequently than would a higher concentration solution of the same drug, were it possible to make such a solution.

Use of dilute solutions of oxazolidinones is disclosed in U.S. Pat. No. 6,337,329 B1 (International counterpart published as WO 00/03710), incorporated herein by reference. The patent, specifically, discloses a method of treating bacterial keratitis or bacterial conjunctivitis in an eye, comprising topical administration of an oxazolidinone antibiotic to the infected eye. Preferred oxazolidinone compounds for use according to the method of WO 00/03710 include (S)-N-[[3-[3-fluoro-4-(4-morpholinyl)phenyl]-2-oxo-5-oxazolidinyl]methyl]acetamide (linezolid) and (S)-N-[[3-[3-fluoro-4-[4-(hydroxyacetyl)-1-piperazinyl]phenyl]-2-oxo-5-oxazolidinyl]methyl]acetamide (eperezolid). The oxazolidinone compound is said to be administered in a formulation such as a solution, cream, ointment, emulsion, suspension or slow release formulation, a solution being preferred. Ophthalmic formulations exemplified therein include 10% and 12% weight/volume solutions of linezolid. At such low concentrations of linezolid, it is further disclosed in U.S. Pat. No. 6,337,329 B1 that the oxazolidinone compound can be used individually, in combination with another oxazolidinone compound, in combination with other antibacterial agents, or in combination with non-antibacterial agents.

International Patent Publication No. WO 00/18387, incorporated herein by reference, discloses additional dilute aqueous ophthalmic compositions comprising an oxazolidinone antimicrobial agent. Preferred oxazolidinone compounds according to WO 00/18387 are those of above-cited U.S. Pat. No. 5,627,181. The oxazolidinone component of the compositions was disclosed to typically be present in a concentration of from about 0.1 to about 1.0 percent by weight of the composition (p. 8). The international patent publication also disclosed that the compositions can further comprise an anti-inflammatory agent.

Where ophthalmic administration of an oxazolidinone antibiotic drug is contemplated, it is desired to be able to administer a pharmaceutically effective dose in as small a volume as possible, without having anything in the ophthalmic solution likely to irritate the eye. It will readily be understood that it is difficult to achieve such concentrations by administration of a relatively small volume of a composition wherein the drug is present in dissolved form, unless the composition has a relatively high drug loading, and in particular a drug loading substantially above the limit of solubility in water of most oxazolidinone antibiotics not in the form of a salt.

Derivatives of cyclodextrin, including α-, β, and γ-cyclodextrins and derivatives thereof, such as ether and mixed ether derivatives, and derivatives bearing sugar residues have been disclosed as being suitable for use in the solubilization of various drugs that are only sparingly soluble in water. EP 0149 197 B2 (Canadian counterpart, CA 1222697) discloses the suitability of partially etherified β-cyclodextrin and derivatives thereof, including hydroxyethyl, hydroxypropyl, and hydroxypropyl-methyl-β cyclodextrin for the solubilization of various types of drugs which are instable or only sparingly soluble in water. None of the drugs disclosed by EP 0149 197 B2 as having been solubilized with one or more of the partially etherified β-cyclodextrins was an antibiotic, much less an oxazolidinone. Likewise, U.S. Pat. No. 4,727,064 discloses the use of hydroxypropyl-β-cyclodextrin and the use of mixtures of that cyclodextrin derivative, diethylaminoethyl-β-cyclodextrin, carboxymethyl-β-cyclodextrin, and carboxamidomethyl-β-cyclodextrin to assist in the dissolution of drugs, but does not disclose the solibilization of any oxazolidinone using such a solubility enhancer. Various sulfoalkyl ether cyclodextrin derivatives, including sulfobulylether-β-cyclodextrin, and their utility in solubilizing certain active agents are disclosed in U.S. Pat. Nos. 5,134,127; 5,376,645. Uses of such sulfoalkyl ether cyclodextrin derivatives in solubilizing additional active agents are disclosed in U.S. Pat. Nos. 5,134,127, 5,874,418; 6,046, 177; and 6,133,248.

Multi-dose formulations, including ophthalmic formulations, typically contain preservatives in order to maintain sterility after opening and during use. U.S. Pat. No. 5,985,310 notes problems with cyclodextrins inactivating the antimicrobial activity of quaternary ammonium compounds and other preservatives pharmaceutical compositions containing cyclodextrins. That patent discloses the use of certain preservatives, including benzalkonium halide compounds, polymeric quaternary ammonium compounds, and quaternary ammonium alkylene glycol phospholipid derivatives that do not interact with cyclodextrins in a way that significantly reduces or eliminates their antimicrobial preservative activity in a solution containing cyclodextrins.

WO 97/10805 notes a similar negative impact of cyclodextrins on quaternary ammonium salt preservatives in aqueous ophthalmic solutions. WO 97/10805 discloses a means of eliminating this negative impact on such preservatives by including an alkylene glycol in aqueous ophthalmic solutions containing cyclodextrin or a cyclodextrin derivative, and a quaternary ammonium salt preservative. Many different drugs are listed as being suitable for use in such formulations, however, none are oxazolidinones.

The references above indicate that cyclodextrins and derivatives thereof can be suitable for solubilization of a variety of different drugs with low solubility. The references summarized above also indicate that when preservatives are included in solutions containing cyclodextrins, at least some preservatives interact with the cyclodextrins in such a way as to inhibit the effectiveness of the preservatives. Even preservatives or preservative systems that do not react with the cyclodextrin component of a formulation could react with an eye upon administration, or with other components of the formulation. None of the references described above disclose any formulation of an oxazolidinone antibiotic drug and a cyclodextrin compound, much less such an oxazolidinone formulation suitable for ophthalmic delivery.

A need, therefore, exists for a solution composition of an oxazolidinone antibiotic drug having a drug loading substantially in excess of the practical limit of solubility of the drug in water. A particular need exists for an ophthalmically deliverable solution composition of an oxazolidinone antibiotic drug having a relatively high concentration of the drug and a solubilization agent, such as a cyclodextrin or derivative thereof, but without any preservative likely to react with an eye upon administration thereto or with other components of the composition.

These and other needs will be seen to be met by the invention now described.

SUMMARY OF THE INVENTION

The present invention provides a preservative free pharmaceutical composition suitable for topical administration to an eye, the composition comprising: (a) an oxazolidinone antibiotic drug in a concentration effective for treatment or prophylaxis of a gram-positive bacterial infection of at least one tissue of the eye, the concentration being above the practical limit of solubility of the drug in an aqueous solution at a physiologically compatible pH; and (b) a pharmaceutically acceptable cyclodextrin compound at a cyclodextrin concentration sufficient to maintain the drug in solution at the drug concentration.

It is believed, without being bound by theory, that the enhanced solubility of the oxazolidinone drug in a composition of the invention is due to association of at least a portion of the drug with the cyclodextrin. It is further believed that at least one mechanism by which the drug associates with the cyclodextrin compound to enhance solubility of the drug in an aqueous medium is through formation of an inclusion complex. Such complexes or conjugates are known in the art to form with a variety of drugs, and a number of advantages have been postulated for use of cyclodextrin-drug complexes in pharmacy. See for example review articles by Bekers et al. (1991) in *Drug Development and Industrial Pharmacy* 17: 1503–1549; Szejtli (1994) in *Medical Research Reviews* 14: 353–386; and Zhang & Rees (1999) in *Expert Opinion on Therapeutic Patents* 9: 1697–1717.

It is also believed, without being limited by theory, that the interaction between the cyclodextrin compound and the oxazolidinone antimicrobial drug in the compounds of the invention is further enabled by the lack of preservatives in solution that can interact with the cyclodextrin compound and inhibit its solubilization of the antimicrobial drug.

Formulations of various drugs with various cyclodextrins have been proposed in the patent literature, including the patents and publications referenced below.

U.S. Pat. No. 5,670,530 to Chen & Shishido discloses compositions comprising a rhodacyanine anti-cancer agent and a cyclodextrin.

U.S. Pat. No. 5,756,546 to Pirotte et al. discloses compositions comprising nimesulide and a cyclodextrin.

U.S. Pat. No. 5,807,895 to Stratton et al. discloses compositions comprising a prostaglandin and a cyclodextrin.

U.S. Pat. No. 5,824,668 to Rubinfeld et al. discloses compositions comprising a 5β steroid drug and a cyclodextrin.

International Patent Publication No. WO 96/32135 discloses compositions comprising propofol and a cyclodextrin.

International Patent Publication No. WO 96/38175 discloses compositions comprising an antiulcerative benzimidazole compound and a branched cyclodextrin-carboxylic acid.

International Patent Publication No. WO 97/39770 discloses compositions comprising a thrombin inhibitor and a cyclodextrin.

International Patent Publication No. WO 98/37884 discloses compositions comprising a 3,4-diarylchroman compound and a cyclodextrin.

International Patent Publication No. WO 98/55148 discloses compositions comprising a sparingly water-soluble drug, a cyclodextrin, a water-soluble acid and a water-soluble organic polymer.

International Patent Publication No. WO 98/58677 discloses compositions comprising voriconazole and a cyclodextrin.

International Patent Publication No. WO 99/24073 discloses compositions comprising a taxoid such as paclitaxel or docetaxel and a cyclodextrin.

International Patent Publication No. WO 99/27932 discloses compositions comprising an antifungal compound of defined formula and a cyclodextrin.

However, the degree of enhancement of solubility achievable through complexation with cyclodextrins of a particular drug or class of drugs is not generally predictable. Cyclodextrins are expensive excipients and in many cases the degree of enhancement of solubility, or other benefit obtained, has not economically justified the increased cost of a formulation arising from addition of a cyclodextrin. The present invention is based in part on the discovery that addition of a relatively modest 4 amount of a cyclodextrin compound, in a preservative free solution, increases the solubility of an oxazolidinone antibiotic drug to a surprising degree. This enhancement in solubility, among other benefits, makes it possible for the first time to ophthalmically deliver a therapeutically or prophylactically effective dose of the oxazolidinone in a minimal number of doses.

As used herein, term "preservative free" refers to the fact that no detectable amount of preservative is found to be present in a solution, such as the composition of the present invention.

The term "pharmaceutically acceptable" in relation to a cyclodextrin or other excipient herein means having no persistent detrimental effect on the eye or general health of the subject being treated. The pharmaceutical acceptability of a cyclodextrin depends, among other factors, on the particular cyclodextrin compound in question, on its concentration in the administered composition, and on the route of administration. For example, use of β-cyclodextrin as an excipient in intravenous compositions is limited by hemolytic and nephrotoxic effects, but is generally non-toxic when administered orally.

The term "practical limit of solubility" in relation to a drug means the highest concentration at which the drug can be formulated in solution without risk of precipitation or crystallization of the drug during the normal range of manufacturing, packaging, storage, handling and use conditions. Typically, the practical limit of solubility is considerably lower than the true solubility limit in a given aqueous medium, for example about 70% of the true solubility limit. Thus, illustratively, for a drug having a true solubility limit in a given aqueous medium of 2.9 mg/ml, the practical limit of solubility is likely to be about 2 mg/ml.

Except where the context demands otherwise, use of the singular herein will be understood to embrace the plural. For example, by indicating above that a composition of the invention comprises "an oxazolidinone antibiotic drug" and "a pharmaceutically acceptable cyclodextrin compound", it will be understood that the composition can contain one or more such drugs and one or more such cyclodextrin compounds.

In one embodiment, present invention provides a method of treating an existing bacterial infection in the eye of a subject, comprising ophthalmically administering a therapeutically effective dose of the preservative free pharmaceutical composition, as described above. Infective diseases of the eye for which compositions and methods of the invention are useful include without limitation conjunctivitis, keratitis, blepharitis, blepharoconjunctivitis, orbital and preseptal cellulitis and endophthalmitis. In preferred methods the infected tissue is one that is directly bathed by the lacrimal fluid, as in conjunctivitis, keratitis, blepharitis and blepharoconjunctivitis.

In infective diseases of the eye where the causal organism is non-bacterial, there can be benefit in prophylactic use of a composition of the invention to control secondary bacterial infections. Examples of such situations include conjunctivitis and keratitis of viral etiology, e.g., adenoviral conjunctivitis, molluscum contagiosum, herpes simplex conjunctivitis and keratitis, etc., and fungal keratitis.

Prophylactic uses of a composition of the invention also include post-traumatic prophylaxis, especially post-surgical prophylaxis, and prophylaxis prior to ocular surgery.

What constitutes a "concentration effective for treatment and/or prophylaxis of a gram-positive bacterial infection" depends, among other factors, on the particular oxazolidinone compound or compounds being administered; the residence time provided by the particular formulation of the active agent; the species, age and body weight of the subject; the particular ophthalmic condition for which treatment or prophylaxis is sought; and the severity of the condition. In the case of linezolid, an effective concentration in a composition of the invention for topical administration to an eye will generally be found in the range from about 0.1 mg/ml to about 100 mg/ml more typically about 0.5 mg/ml to about 80 mg/ml. For oxazolidinone compounds other than linezolid, an appropriate concentration range is one that is therapeutically equivalent to the linezolid concentration range indicated above.

The term "ophthalmically acceptable" with respect to a formulation, composition or ingredient herein means having no persistent detrimental effect on the treated eye or the functioning thereof, or on the general health of the subject being treated. It will be recognized that transient effects such as minor irritation or a "stinging" sensation are common with topical ophthalmic administration of drugs and the existence of such transient effects is not inconsistent with the formulation, composition or ingredient in question being "ophthalmically acceptable" as herein defined. However, preferred formulations, compositions and ingredients are those that cause no substantial detrimental effect, even of a transient nature.

Contemplated compositions are highly effective in treating gram-positive bacterial infections of the eye. Without being bound by theory, it is believed that the high concentration of oxazolidinone, facilitated by the presence of a cyclodextrin or derivative thereof, and the absence of any preservative likely to degrade or interfere with the cyclodextrin enable one to deliver a higher amount of an oxazolidinone antibiotic drug to ophthalmic tissues where it is needed most than is possible with existing formulations. Thus, one could treat or prevent bacterial infections or other conditions of an eye cited by treating the eye according to the method of the present invention.

Other advantages of the present invention will become apparent from the following description of the invention and Examples, below.

DETAILED DESCRIPTION OF THE INVENTION

Figure 1:
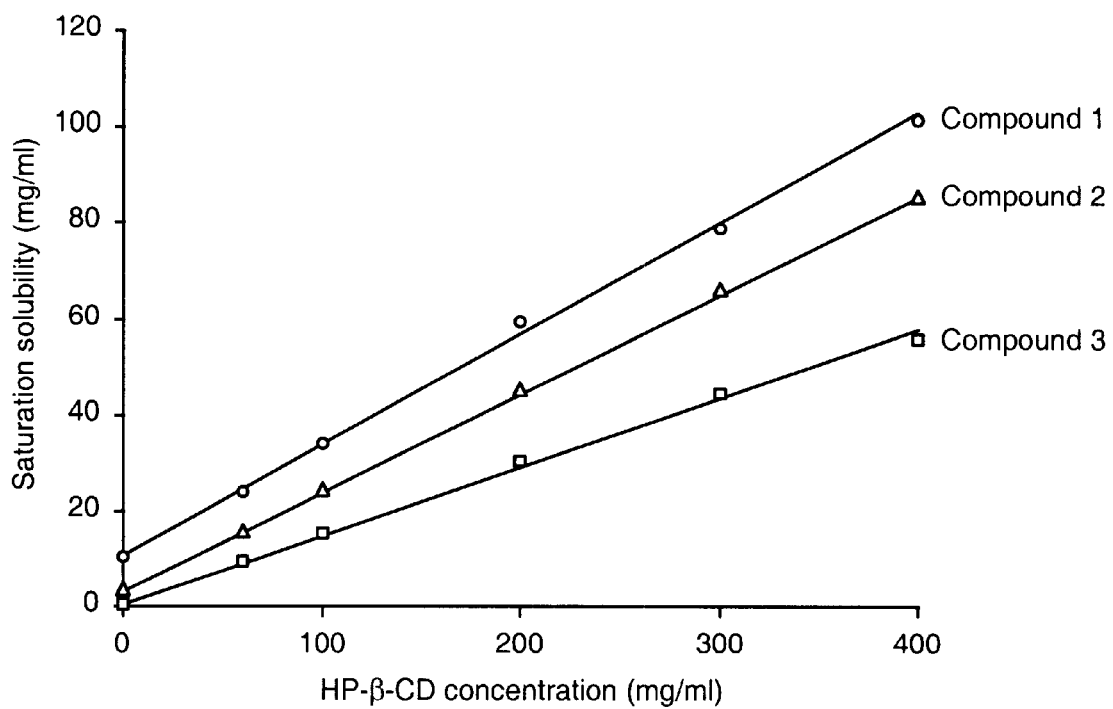
FIG. 1 is a graphical representation of data from the study described in Example 5 herein, and demonstrates enhanced saturation solubility of oxazolidinone compounds in aqueous solutions containing hydroxypropyl-β-cyclodextrin (HP-β-CD).

Any oxazolidinone antimicrobial drug, i.e., one having an oxazolidinone moiety as part of its chemical structure, can be formulated with a cyclodextrin compound in accordance with the invention. In a preferred embodiment, the oxazolidinone drug is a compound of formula (II)

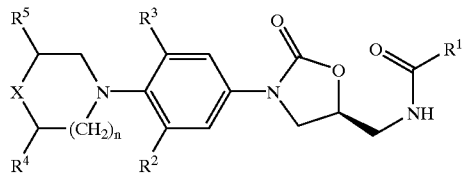

(II)

wherein:
R$^1$ is selected from (a) H, (b) C$_{1-8}$ alkyl optionally substituted with one or more F, Cl, OH, C$_{1-8}$ alkoxy, C$_{1-8}$ acyloxy or benzoxy groups, and including C$_{3-6}$ cycloalkyl, (c) amino, (d) mono- and di(C$_{1-8}$ alkyl) amino and (e) C$_{1-8}$ alkoxy groups;

R$^2$ and R$^3$ are independently selected from H, F and Cl groups;

R$^4$ is H or CH$_3$;

R$^5$ is selected from H, CH$_3$, CN, CO$_2$R$^1$ and (CH$_2$)$_m$R$^6$ groups, where R$^1$ is as defined above, R$^6$ is selected from H, OH, OR$^1$, OCOR$^1$, NHCOR$^1$, amino, mono- and di(C$_{1-8}$ alkyl)amino groups and m is 1 or 2;

n is 0, 1 or 2; and

X is O, S, SO, SO$_2$, SNR$^7$ or S(O)NR$^7$ where R$^7$ is selected from H, C$_{1-4}$ alkyl (optionally substituted with one or more F, Cl, OH, C$_{1-8}$ alkoxy, amino, C$_{1-8}$ mono- or di(C$_{1-8}$ alkyl)amino groups), and p-toluenesulfonyl groups; or a pharmaceutically acceptable salt thereof.

Particularly preferred oxazolidinone drugs according to this embodiment are compounds of formula (II) wherein R$^1$ is CH$_3$; R$^2$ and R$^3$ are independently selected from H and F but at least one of R$^2$ and R$^3$ is F; R$^4$ and R$^5$ are each H; n is 1; and X is O, S or SO$_2$. In another preferred embodiment, the oxazolidinone drug is selected from linezolid, eperezolid, N-((5S)-3-(3-fluoro-4-(4-(2-fluoroethyl)-3-oxopiperazin-1-yl)phenyl)-2-oxooxazolidin-5-ylmethyl) acetamide, (S)-N-[[3-[5-(3-pyridyl)thiophen-2-yl]-2-oxo-5-oxazolidinyl]methyl]acetamide, (S)-N-[[3-[5-(4-pyridyl) pyrid-2-yl]-2-oxo-5-oxazolidinyl]methyl]acetamide hydrochloride and N-[[(5S)-3-[4-(1,1-dioxido-4-thiomorpholinyl)-3,5-diflourophenyl]-2-oxo-5-oxazolidinyl]methyl]acetamide.

According to either of these preferred embodiments, an especially preferred oxazolidinone drug is linezolid. Another especially preferred oxazolidinone drug is N-[[(5S)-3-[4-(1, 1-dioxido-4-thiomorpholinyl)-3,5-difluorophenyl]-2-oxo-5-oxazolidinyl]methyl]acetamide. The invention is illustrated herein with particular reference to linezolid, and it will be understood that any other oxazolidinone antibacterial compound can, if desired, be substituted in whole or in part for linezolid, with appropriate adjustment in concentration and dosage ranges, in the compositions and methods herein described.

Oxazolidinone compounds used in compositions of the invention can be prepared by a process known per se, in the case of linezolid and eperezolid, for example, by processes described in the following patents, each of which is individually incorporated herein by reference.

U.S. Pat. No. 5,688,791.

U.S. Pat. No. 5,837,870.

International Patent Publication No. WO 99/24393.

Other oxazolidinone drugs can be prepared by processes known per se, including processes set forth in patent publications disclosing such drugs.

The invention is illustrated herein with particular reference to linezolid, and it will be understood that any other oxazolidinone antimicrobial drug can, if desired, be substituted in whole or in part for linezolid, with appropriate adjustment in concentration and dosage ranges, in the compositions and methods herein described.

Linezolid is usefully present in a composition of the invention at a concentration of about 3 mg/ml to as high a concentration as is practically enabled by the cyclodextrin present therewith, for example about 100 mg/ml. In a composition intended for direct administration as formulated, the concentration of linezolid is preferably about 0.1 to about 100 mg/ml, more preferably about 0.5 to about 80 mg/ml, even more preferably about 10 mg/ml to about 60 mg/ml, for example about 50 mg/ml. Useful concentrations of other oxazolidinone drugs are those that are therapeutically equivalent to the linezolid concentration ranges given immediately above.

The cyclodextrin compound with which the oxazolidinone antibiotic drug is formulated according to the present invention is preferably selected from α-cyclodextrin, β-cyclodextrin, γ-cyclodextrin, alkylcyclodextrins (e.g., methyl-β-cyclodextrin, dimethyl-β-cyclodextrin, diethyl-β-cyclodextrin), hydroxyalkylcyclodextrins (e.g., hydroxyethyl-β-cyclodextrin, hydroxypropyl-β-cyclodextrin), carboxyalkylcyclodextrins (e.g., carboxymethyl-β-cyclodextrin) and sulfoalkylether cyclodextrins (e.g., sulfobutylether-β-cyclodextrin). More preferred are hydroxyalkyl-β-cyclodextrins and sulfoalkylether-β-cyclodextrins; still more preferred are hydroxypropyl-β-cyclodextrin and sulfobutylether-β-cyclodextrin.

If desired, complexation of an oxazolidinone antibiotic drug by a cyclodextrin can be increased by addition of a water-soluble polymer such as carboxymethylcellulose or a salt thereof, hydroxypropylmethylcellulose or polyvinylpyrrolidone, as described by Loftsson (1998), *Pharmazie* 53: 733–740.

The cyclodextrin is present at a concentration effective to enhance the solubility of the oxazolidinone, for example at a concentration of about 1 to about 500 mg/ml. In practice and in view of the high cost of cyclodextrins, the amount of the cyclodextrin present in a composition of the invention is preferably only slightly greater, for example no more than about 50% greater, than a minimum amount required to maintain the oxazolidinone in solution at the desired oxazolidinone concentration.

Where the composition is intended for direct administration to an eye as formulated, the concentration of cyclodextrin in the composition is preferably from about 1 to about 500 mg/ml, more preferably about 5 to about 300 mg/ml, more preferably about 5 to about 250 mg/ml, even more preferably about 10 mg/ml to about 100 mg/ml.

The composition is preferably in the form of an aqueous solution, more preferably, one that can be presented in the form of eye drops. By means of a suitable dispenser, a desired dosage of the active agent can be metered by administration of a known number of drops into the eye, and most preferably by one drop. Suitable dispensers are illustratively disclosed in International Patent Publication No. WO 96/06581, incorporated herein by reference.

The composition of the invention optionally further includes at least one ophthalmically acceptable pH adjusting agent and/or buffer, including an acid such as acetic, boric, citric, lactic, phosphoric and hydrochloric acids; a base such as sodium hydroxide, sodium phosphate, sodium borate, sodium citrate, sodium acetate, sodium lactate and tris-hydroxymethylaminomethane, triethanolamine; and a buffer such as citrate/dextrose, sodium bicarbonate and ammonium chloride, or an amino acid. Such an acid, base and/or buffer is preferably included in an amount required to maintain pH of the composition in an ophthalmically acceptable range.

The composition optionally further includes at least one ophthalmically acceptable salt in an amount required to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions; preferred salts include sodium chloride, potassium chloride, sodium thiosulfate, sodium bisulfite and ammonium sulfate, with sodium chloride being especially preferred. Other solutes suitable for adjustment of osmolality include sugars, for example dextrose, lactose, xylitol, mannitol and glycerine.

Accordingly, a particular embodiment of the invention is a composition as described hereinabove, further comprising a buffering agent and/or an agent for adjusting osmolality in amounts whereby the solution is substantially isotonic and has a physiologically acceptable pH.

A challenge for topical administration of drugs to the eye is a high rate of drug loss from the exterior of the eye. Only a small volume of fluid can be accommodated in the exterior of the eye, including the conjunctival sac, and under normal conditions lacrimal fluid fills most of the available volume. The additional volume of fluid in the form of a drug formulation that can be accepted by a human eye without washout varies from about 3 µl to about 25 µl, but is normally about 10 µl. Furthermore, turnover rate of lacrimal fluid is high, typically about 16% per minute, and this can lead to rapid loss of an instilled drug by normal lacrimal drainage. Thus under normal conditions, only about 10% to about 20% of a drug dose is retained in the exterior of the eye 5 minutes after placement therein of 1–2 drops of a solution or suspension composition of the drug, and the composition is almost completely eliminated within 15 minutes. See for example Sorensen & Jensen (1979), *Acta Ophthalmol.* (Copenhagen) 57, 564–581. Reflex blinking and lacrimation caused by irritation from the topical administration can result in even faster drug loss.

Increasing viscosity of the instilled formulation and hence of the lacrimal fluid can reduce the rate of lacrimal drainage and thereby increase residence time of the drug in the exterior of the eye. A consequence of removal of an ophthalmic composition from a treated eye is a reduced concentration of the active agent in the lacrimal fluid and hence in the target tissue. Ointments are often used as ophthalmic formulations for this reason. However, ointments often cause discomfort by interfering with vision and free movement of the eyelids. Clear aqueous solutions and suspensions are therefore usually a preferred choice, especially for daytime administration. The ophthalmic composition of the present invention can be in the form of an ointment. However, it is preferably in the form of an aqueous solution or suspension, more preferably in the form of a clear aqueous solution.

The composition of the present invention preferably further includes at least one ophthalmically acceptable excipient ingredient that reduces the rate of removal of the composition from the eye by lacrimation, such that the composition has an effective residence time in the eye of about 2 to about 24 hours. Lacrimation is the production of tear fluid, and can remove matter from the eyes both by external wash-out and by lacrimal drainage into the nasopharyngeal cavity via the nasolacrimal ducts. A consequence of removal of an ophthalmic composition from a treated eye is a reduced concentration of the active agent in the lacrimal fluid and hence in the target tissue.

For sustained antibacterial action, the concentration in the lacrimal fluid and in the target tissue, e.g., the conjunctiva or the cornea, must remain above the $MIC_{90}$ for the active agent in question. The $MIC_{90}$ is the minimum inhibitory concentration for 90% of the target organisms, in this instance infective gram-positive bacteria. For example, where the active agent is linezolid, the $MIC_{90}$ is about 4 µg/ml. By "effective residence time" herein is meant a period of time following application of the composition to the eye during which the concentration of the active agent in the lacrimal fluid and/or in the target tissue remains above the $MIC_{90}$ for that active agent.

The aqueous suspension or solution of the present invention is preferably viscous or mucoadhesive, or even more preferably, both viscous or mucoadhesive. In a particularly preferred embodiment, the aqueous suspension or solution/suspension of the invention contains carboxymethylcellulose, a viscosity enhancer and promoter of mucoadhesion. The concentration of carboxymethylcellulose in the aqueous suspension or solution of the present invention is preferably 0.1% to 5%, more preferably about 0.1% to about 2.5% by weight. The carboxymethylcellulose is preferably in the form of sodium carboxymethylcellulose substituted to a degree that the sodium content of the sodium carboxymethylcellulose is about 1% to about 20%.

Preferably no more than 3 drops, more preferably no more than 2 drops, and most preferably no more than 1 drop, each of about 10 to about 40 µl, preferably about 15 to about 30 µl, for example about 20 µl, should contain the desired dose of the active agent for administration to an eye. Administration of a larger volume to the eye risks loss of a significant portion of the applied composition by lacrimal drainage.

Any one of a number of different excipients can be included in the composition of the present invention to increase retention of the composition in an eye. For example, any ophtalmically compatable viscosity enhancer can be included in the composition of the present invention. An alternative class of excipients suitable for use in the compositions of the present invention are disclosed in U.S. Pat. No. 4,474,751 to Haslam et al., incorporated herein by reference, that describes liquid aqueous ophthalmic compositions comprising a drug, preferably a water-soluble drug, together with 10% to 50% by weight of a thermosetting polymer that forms a gel at a human body temperature. Upon placement of such a liquid composition in an eye, a gel is said to form thereby retarding loss of the drug from the eye by lacrimal drainage. Such compositions are said to be useful for ophthalmic delivery of antibacterial agents, for example vancomycin.

In a preferred embodiment, the composition is an in situ gellable aqueous composition, more preferably an in situ gellable aqueous solution. Such a composition comprises a gelling agent in a concentration effective to promote gelling upon contact with the eye or with lacrimal fluid in the exterior of the eye. Suitable gelling agents non-restrictively include thermosetting polymers such as tetra-substituted ethylene diamine block copolymers of ethylene oxide and propylene oxide (e.g., poloxamine 1307); polycarbophil; and polysaccharides such as gellan, carrageenan (e.g., kappa-carrageenan and iota-carrageenan), chitosan and alginate gums.

The term "in situ gellable" herein is to be understood as embracing not only liquids of low viscosity that form gels upon contact with the eye or with lacrimal fluid in the exterior of the eye, but also more viscous liquids such as semi-fluid and thixotropic gels that exhibit substantially increased viscosity or gel stiffness upon administration to the eye. Indeed, it can be advantageous to formulate a composition of the invention as a gel, to minimize loss of the composition immediately upon administration, as a result for example of lacrimation caused by reflex blinking. Although it is preferred that such a composition exhibit further increase in viscosity or gel stiffness upon administration, this is not absolutely required if the initial gel is sufficiently resistant to dissipation by lacrimal drainage to provide the effective residence time specified herein.

Any one of a number of in situ gelling excipients or systems are suitable for use in the composition of the present invention, including but not limited to the following.

U.S. Pat. No. 4,861,760 to Mazuel & Friteyre, incorporated herein by reference, discloses a liquid in situ gelling composition said to be suitable for ophthalmic use. The composition contains in aqueous solution a polysaccharide that undergoes liquid-gel phase transition in response to ionic strength of tear fluid. A suitable polysaccharide is gellan gum, which can be used in a concentration of 0.1% to 2% by weight of the composition. Such a composition is said to be useful for ophthalmic delivery of antibacterial agents, for example vancomycin.

In a particularly preferred embodiment, the composition is an in situ gellable aqueous solution, suspension or solution/suspension having excipients substantially as disclosed in above-cited U.S. Pat. No. 4,861,760, comprising about 0.1% to about 2% by weight of a polysaccharide that gels when it contacts an aqueous medium having the ionic strength of lacrimal fluid. A preferred such polysaccharide is gellan gum, more preferably a low acetyl clarified grade of gellan gum such as that sold under the trademark Gelrite®. Suitable partially deacylated gellan gums are disclosed in U.S. Pat. No. 5,190,927 to Chang & Kobzeff, incorporated herein by reference. Preferably the drug is in solution in the composition.

In another particular embodiment the composition is an in situ gellable aqueous solution, suspension or solution/suspension having excipients substantially as disclosed in above-cited U.S. Pat. No. 5,587,175, comprising about 0.2% to about 3%, preferably about 0.5% to about 1%, by weight of a gelling polysaccharide, preferably selected from gellan gum, alginate gum and chitosan, and about 1% to about 50% of a water-soluble film-forming polymer, preferably selected from alkylcelluloses (e.g., methylcellulose, ethylcellulose), hydroxyalkylcelluloses (e.g., hydroxyethylcellulose, hydroxypropyl methylcellulose), hyaluronic acid and salts thereof, chondroitin sulfate and salts thereof, polymers of acrylamide, acrylic acid and polycyanoacrylates, polymers of methyl methacrylate and 2-hydroxyethyl methacrylate, polydextrose, cyclodextrins, polydextrin, maltodextrin, dextran, polydextrose, gelatin, collagen, natural gums (e.g., xanthan, locust bean, acacia, tragacanth and carrageenan gums and agar), polygalacturonic acid derivatives (e.g., pectin), polyvinyl alcohol, polyvinylpyrrolidone and polyethylene glycol. The composition can optionally contain a gel-promoting counterion such as calcium in latent form, for example encapsulated in gelatin. Preferably the drug is in solution in the composition.

In a particularly preferred embodiment, the composition is an in situ gellable aqueous solution, suspension or solution/suspension having excipients substantially as disclosed in above-cited U.S. Pat. No. 4,861,760, comprising about 0.1% to about 2% by weight of a polysaccharide that gels when it contacts an aqueous medium having the ionic strength of lacrimal fluid. A preferred such polysaccharide is gellan gum, more preferably a low acetyl clarified grade of gellan gum such as that sold under the trademark Gelrite®. Suitable partially deacylated gellan gums are disclosed in U.S. Pat. No. 5,190,927 to Chang & Kobzeff, incorporated herein by reference. Preferably the drug is in solution in the composition.

A challenge for topical administration of drugs to the eye is a high rate of drug loss from the exterior of the eye. Only a small volume of fluid can be accommodated in the exterior of the eye, including the conjunctival sac, and under normal conditions lacrimal fluid fills most of the available volume. The additional volume of fluid in the form of a drug formulation that can be accepted by a human eye without washout varies from about 3 μl to about 25 μl, but is normally about 10 μl. Furthermore, turnover rate of lacrimal fluid is high, typically about 16% per minute, and this can lead to rapid loss of an instilled drug by normal lacrimal drainage. Thus under normal conditions, only about 10% to about 20% of a drug dose is retained in the exterior of the eye 5 minutes after placement therein of 1–2 drops of a solution or suspension composition of the drug, and the composition is almost completely eliminated within 15 minutes. See for example Sorensen & Jensen (1979), *Acta Ophthalmol.* (Copenhagen) 57, 564–581. Reflex blinking and lacrimation caused by irritation from the topical administration can result in even faster drug loss.

U.S. Pat. No. 5,192,535 to Davis et al., incorporated herein by reference, discloses liquid compositions said to be suitable for use as eye drops, utilizing a different in situ gelling mechanism. These compositions contain a lightly cross-linked carboxyl-containing polymer such as polycarbophil and have a pH of about 3.0 to about 6.5. Upon placement of such a composition in an eye, contact with lacrimal fluid having a pH of about 7.2 to about 7.4 is said to result in gelling and consequent increase of residence time in the eye, permitting sustained release of a drug contained in the composition. Drugs for which such a composition is said to be useful include antibiotics, for example vancomycin.

In a particularly preferred embodiment, the composition is an in situ gellable aqueous solution having excipients substantially as disclosed in above-cited U.S. Pat. No. 5,192,535, comprising about 0.1% to about 6.5%, preferably about 0.5% to about 4.5%, by weight, based on the total weight of the composition, of one or more lightly cross-linked carboxyl-containing polymers, and preferably having the oxazolidinone drug in solution. Such an aqueous composition has a pH of about 3 to about 6.5, preferably about 4 to about 6. A preferred polymer in this embodiment is polycarbophil, which causes the composition to gel upon contact with lacrimal fluid in the eye, which has a typical pH of about 7.2 to about 7.4. This formation of a gel enables the composition to remain in the eye for a prolonged period without loss by lacrimal drainage.

U.S. Pat. No. 5,212,162 to Missel et al., incorporated herein by reference, discloses further liquid in situ gelling compositions said to be suitable for ophthalmic use. The compositions contain a drug together with a finely-divided (conveniently about 1 to about 25 µm particle size) carrier that binds with the drug, and a gelling polysaccharide, preferably a carrageenan, especially a carrageenan having not more than 1.0 sulfate moiety per disaccharide unit, e.g., eucheuma carrageenan, kappa-carrageenan or furcellaran. Such compositions are said to be useful for ophthalmic delivery of anti-infective agents, for example ciprofloxacin.

U.S. Pat. No. 5,403,841 to Lang et al., incorporated herein by reference, discloses further liquid in situ gelling compositions said to be suitable for ophthalmic use. These compositions contain a carrageenan having not more than 1.0 sulfate moiety per disaccharide unit that is capable of gelling in 0.5% to 1.0% aqueous sodium chloride solution. Such compositions are said to be useful for ophthalmic delivery of anti-infective agents, for example ciprofloxacin.

U.S. Pat. No. 5,587,175 to Viegas et al., incorporated herein by reference, discloses further liquid in situ gelling compositions said to be suitable for ophthalmic use. These compositions contain an ionic polysaccharide, for example gellan gum, alginate gum or chitosan, and a film-forming agent, for example hydroxypropyl methylcellulose, carboxymethylcellulose, sodium chondroitin sulfate, sodium hyaluronate, polyvinylpyrrolidone, etc. The compositions are pH buffered to match pH of tear fluid. Gelling is said to occur upon contact with calcium ions. Such compositions are said to be useful for ophthalmic delivery of antibacterial agents, for example vancomycin.

U.S. Pat. No. 5,876,744 to Della Valle et al., incorporated herein by reference, discloses bioadhesive and mucoadhesive compositions, including some said to be useful as ophthalmic compositions, comprising mixtures of synthetic polymers such as polycarbophil and polyvinyl alcohol and biopolymers such as alginic acid, hyaluronic acid and dermatan sulfate. Such compositions are said to be capable of increasing contact time with a treated eye of specific drugs.

European Patent No. 0 424 043, incorporated herein by reference, discloses a liquid ophthalmic composition comprising a sulfated polysaccharide or derivative thereof that undergoes a liquid-gel transition on interaction with proteins of the lacrimal fluid in the eye. Such sulfated polysaccharides are said to include kappa-carrageenan, iota-carrageenan and mixtures thereof. The composition is said to be useful for ophthalmic delivery of antibacterial agents.

In another particularly preferred embodiment, the composition is an in situ gellable aqueous solution containing xanthan gum, substantially as disclosed in U.S. Pat. No. 6,174,524.

In another particular embodiment the composition is an in situ gellable aqueous solution excipients substantially as disclosed in above-cited European Patent No. 0 424 043, comprising about 0.1% to about 5% of a carrageenan gum. Carrageenans are sulfated polysaccharides; in this embodiment a carrageenan having no more than 2 sulfate groups per repeating disaccharide unit is preferred, including kappa-carrageenan, having 18–25% ester sulfate by weight, iota-carrageenan, having 25–34% ester sulfate by weight, and mixtures thereof. As indicated above, and contrary to the teaching of above-cited European Patent No. 0 424 043, where a preservative is to be included, it is preferred according to the present invention to select a preservative that does not precipitate in the composition.

In another particular embodiment the composition comprises an ophthalmically acceptable mucoadhesive polymer, selected for example from hydroxypropylmethylcellulose, carboxymethylcellulose, carbomer (acrylic acid polymer), poly(methylmethacrylate), polyacrylamide, polycarbophil, polyethylene oxide, acrylic acid/butyl acrylate copolymer, sodium alginate and dextran.

Optionally, an ophthalmically acceptable xanthine derivative such as caffeine, theobromine or theophylline can be included in the composition, substantially as disclosed in U.S. Pat. No. 4,559,343 to Han & Roehrs, incorporated herein by reference. Inclusion of the xanthine derivative can reduce ocular discomfort associated with administration of the composition.

Optionally, one or more ophthalmically acceptable surfactants, preferably nonionic surfactants, can be included in the composition to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Optionally, one or more antioxidants can be included in the composition to enhance chemical stability where required. Suitable antioxidants include ascorbic acid and sodium metabisulfite.

One or more ophthalmic lubricating agents can optionally be included in the composition to promote lacrimation or as a "dry eye" medication. Such agents include polyvinyl alcohol, methylcellulose, hydroxypropyl methylcellulose, polyvinylpyrrolidone, etc. It will be understood that promotion of lacrimation is beneficial in the present invention only where lacrimation is naturally deficient, to restore a normal degree of secretion of lacrimal fluid. Where excessive lacrimation occurs, residence time of the composition in the eye can be reduced.

A composition of this particular embodiment can optionally further comprise glycerin in an amount of about 0.5% to about 5%, more preferably about 1% to about 2.5%, for example about 1.5% to about 2%, by weight. Glycerin can be useful to increase viscosity of the composition and for adjustment of osmolality. Independently of the presence of glycerin, a composition of this particular embodiment can optionally further comprise a cyclodextrin, preferably hydroxypropyl-$\beta$-cyclodextrin, in an amount of about 1 mg/ml to about 500 mg/ml. Such a cyclodextrin can be useful as a solubilizing agent as described above.

In another embodiment, the composition is either used in co-therapy, co-administration, or coformulated with at least one drug other than an antibacterial agent. In a preferred embodiment, the composition of the present invention further comprises a therapeutically and/or prophylactically effective amount of the at least one drug other than an antibacterial agent. The drug other than an antibacterial agent can cooperate with the oxazolidinone antibacterial drug(s) in the composition in treating and/or preventing an infective disease of the eye, or can be used to treat a related or unrelated condition simultaneously affecting the eye.

Any drug having utility as a topical ophthalmic application can be used in co-therapy, co-administration or coformulation with a composition of the invention as described immediately above. Such drugs include without limitation demulcents; antimycotics, antivirals and other anti-infectives; steroids, NSAIDs, selective cyclooxygenase-2 inhibitors and other anti-inflammatory agents; acetylcholine blocking agents; adrenergic agonists, beta-adrenergic blocking agents and other antiglaucoma agents; antihypertensives; antihistamines; anticataract agents; and topical and regional anesthetics. Illustrative specific drugs include acebutolol, aceclidine, acetylsalicylic acid (aspirin), $N^4$ acetylsulfisoxazole, alclofenac, alprenolol, amfenac, amiloride, aminocaproic acid, p-aminoclonidine, aminozolamide, anisindione, apafant, atenolol, bacitracin, benoxaprofen, benoxinate, benzofenac, bepafant, betamethasone, betaxolol, bethanechol, brimonidine, bromfenac, bromhexine, bucloxic acid, bupivacaine, butibufen, carbachol, carprofen, celecoxib, cephalexin, chloramphenicol, chlordiazepoxide, chlorprocaine, chlorpropamide, chlortetracycline, cicloprofen, cinmetacin, ciprofloxacin, clidanac, clindamycin, clonidine, clonixin, clopirac, cocaine, cromolyn, cyclopentolate, cyproheptadine, demecarium, dexamethasone, dibucaine, diclofenac, diflusinal, dipivefrin, dorzolamide, enoxacin, epinephrine, erythromycin, eserine, estradiol, ethacrynic acid, etidocaine, etodolac, fenbufen, fenclofenac, fenclorac, fenoprofen, fentiazac, flufenamic acid, flufenisal, flunoxaprofen, fluorocinolone, fluorometholone, flurbiprofen and esters thereof, fluticasone propionate, furaprofen, furobufen, furofenac, furosemide, gancyclovir, gentamicin, gramicidin, hexylcaine, homatropine, hydrocortisone, ibufenac, ibuprofen and esters thereof, idoxuridine, indomethacin, indoprofen, interferons, isobutylmethylxanthine, isofluorophate, isoproterenol, isoxepac, ketoprofen, ketorolac, labetolol, lactorolac, latanoprost, levo-bunolol, lidocaine, lonazolac, loteprednol, meclofenamate, medrysone, mefenamic acid, mepivacaine, metaproterenol, methanamine, methylprednisolone, metiazinic, metoprolol, metronidazole, minopafant, miroprofen, MK-663, modipafant, nabumetome, nadolol, namoxyrate, naphazoline, naproxen and esters thereof, neomycin, nepafenac, nitroglycerin, norepinephrine, norfloxacin, nupafant, olfloxacin, olopatadine, oxaprozin, oxepinac, oxyphenbutazone, oxyprenolol, oxytetracycline, parecoxib, penicillins, perfloxacin, phenacetin, phenazopyridine, pheniramine, phenylbutazone, phenylephrine, phenylpropanolamine, phospholine, pilocarpine, pindolol, pirazolac, piroxicam, pirprofen, polymyxin, polymyxin B, prednisolone, prilocaine, probenecid, procaine, proparacaine, protizinic acid, rimexolone, rofecoxib, salbutamol, scopolamine, sotalol, sulfacetamide, sulfanilic acid, sulindac, suprofen, tenoxicam, terbutaline, tetracaine, tetracycline, theophyllamine, timolol, tobramycin, tolmetin, triamcinolone, trimethoprim, trospectomycin, valdecoxib, vancomycin, vidarabine, vitamin A, warfarin, zomepirac and pharmaceutically acceptable salts thereof.

Compositions of the present invention can be prepared by processes known in the art, including by simple admixture, with agitation as appropriate, of the ingredients. Preferably, an aqueous solution of the cyclodextrin compound is first prepared, and the oxazolidinone in finely divided solid particulate form is added to that solution with agitation until it is fully dissolved. Where it is desired to prepare a buffered isotonic solution buffering agents and agents for adjustment of osmolality can be added at any stage but are preferably present in solution with the cyclodextrin compound before addition of the oxazolidinone. Similarly, where it is desired to include any of the other additional alternative components cited above in the composition they can be added at any stage, but are preferably present in the solution with the cyclodextrin compound before addition of the oxazolidinone. Processes for preparing an ophthalmic composition of the invention are preferably conducted so as to provide a sterile product.

Aqueous suspension compositions of the invention can be packaged in single-dose non-reclosable containers. Such containers can maintain the composition in a sterile condition and thereby eliminate need for preservatives such as mercury-containing preservatives, which can sometimes cause irritation and sensitization of the eye. Alternatively, multiple-dose reclosable containers can be used, in which case it is preferred to include a preservative in the composition.

In a method of the invention for treating or preventing infective disease, an ophthalmic composition as described above in a therapeutically or prophylactically effective dose is administered to at least one eye of a subject in need thereof.

As indicated above, a method of the invention is particularly useful where the infective disease arises through infection by one or more gram-positive bacteria. Where broader-spectrum antibacterial activity, extending to gram-negative bacteria, is required, a second antimicrobial drug can be administered in co-therapy, including for example coformulation, with the present composition. The second antimicrobial drug is selected to be effective against target gram-negative bacteria. Such co-therapy and coformulation are embodiments of the present invention.

The second antimicrobial drug can illustratively be selected from aminoglycosides, cephalosporins, diaminopyridines, fluroquinolones, sulfonamides and tetracyclines. Among particular antimicrobial drugs of these and other classes, each of the following may illustratively be useful as the second antimicrobial drug according to an embodiment of the present invention: amikacin, cefixime, cefoperazone, cefotaxime, ceftazidime, ceftizoxime, ceftriaxone, chloramphenicol, ciprofloxacin, clindamycin, colistin, domeclocycline, doxycycline, gentamicin, mafenide, methacycline, minocycline, neomycin, norfloxacin, ofloxacin, oxytetracycline, polymyxin B, pyrimethamine, silver sulfadiazine, sulfacetamide, sulfisoxazole, tetracycline, tobramycin and trimethoprim.

In a method of the invention, a composition as herein described is administered topically in an antibacterially effective amount to an eye that is infected by one or more gram-positive bacterial organisms. The eye is of a warm-blooded, preferably a mammalian subject. Suitable mammalian subjects include domestic mammals, farm and exotic mammals, and humans. The method can be useful, for example, in treatment of eye infections of dogs, cats, horses, cattle, sheep and pigs, but is more particularly useful where the subject is human.

In a preferred method, the gram-positive bacterial organism(s) are species of Staphylococcus (e.g., *Staphylococcus aureus, Staphylococcus epidermidis*), Streptococcus (e.g., *Streptococcus viridans, Streptococcus pneumoniae*), Enterococcus, Bacillus, Corynebacterium, Propionibacterium, Chlamydia, Moraxella, Haemophilus and Neisseria. In an especially preferred method, the gram-positive bacterial organism(s) are of strain(s) that have developed significant levels of resistance to antibacterial agents other than the oxazolidinone antibacterial agent(s), e.g., linezolid, in the composition being administered.

Treatment of bacterial conjunctivitis by the method of the invention is appropriate, for example, where infection with one or more of the following species is present: *Staphylococcus aureus, Staphylococcus epidermidis, Streptococcus pneumoniae, Streptococcus pyogenes, Streptococcus viridans, Enterococcus faecalis*, Corynebacterium sp., Propionibacterium sp., *Moraxella catarrhalis* and *Haemophilus influenzae*.

Treatment of bacterial blepharitis by the method of the invention is appropriate, for example, where infection with one or more of the following species is present: *Staphylococcus aureus, Staphylococcus epidermidis* and *Streptococcus pneumoniae*.

Treatment of bacterial keratitis by the method of the invention is appropriate, for example, where infection with one or more of the following species is present: *Staphylococcus aureus, Staphylococcus epidermidis, Streptococcus pneumoniae* and *Streptococcus viridans*.

Prophylaxis of bacterial infection of the eye prior to ocular surgery by the method of the invention is appropriate, for example, where a risk exists of infection with one or more of the following species: *Staphylococcus aureus, Staphylococcus epidermidis*, Corynebacterium sp. and Propionibacterium sp.

An appropriate dosage, frequency and duration of administration, i.e., treatment regimen, to be used in any particular situation will be readily determined by one of skill in the art without undue experimentation, and will depend, among other factors, on the particular oxazolidinone compound(s) present in the composition, on the particular ophthalmic infective condition being treated, on the age, weight and general physical condition of the subject, and on other medication being administered to the subject. It is preferred that response of the ophthalmic infective condition to treatment according to the present method be monitored and the treatment regimen be adjusted if necessary in light of such monitoring.

Frequency of administration is typically such that the dosing interval, i.e., the period of time between one dose and the next, during waking hours is about 2 to about 12 hours, more typically about 3 to about 8 hours, for example about 4 to about 6 hours. It will be understood by those of skill in the art that an appropriate dosing interval is dependent to some degree on the length of time for which the selected composition is capable of maintaining a concentration of the oxazolidinone antibiotic in the lacrimal fluid and/or in the target tissue (e.g., the conjunctiva) above the $MIC_{90}$. Ideally the concentration remains above the $MIC_{90}$ for at least 100% of the dosing interval. Where this is not achievable it is desired that the concentration should remain above the $MIC_{90}$ for at least about 60% of the dosing interval, in a less desired case the concentration remains above the $MIC_{90}$ for less than about 60% to as low as about 25% of the dosing interval.

The following examples are illustrative of the process and products of the present invention. They are not to be construed as limiting. All experiments were or are done at room temperature and pressure, unless otherwise indicated.

EXAMPLES

The following Examples illustrate aspects of the present invention but are not to be construed as limitations.

Example 1

A study was conducted to examine solubility of linezolid in an aqueous system containing sulfobutylether-β-cyclodextrin ("SB-β-CD").

Aqueous solutions of SB-β-CD at concentrations of 10, 50, 100, 150, 250 and 500 mg/ml were prepared. Excess linezolid was added to each solution. The solutions were stirred for 24 h at 25° C. and were then filtered using 0.2 μm Gelman Acrodisc filter units and assayed for linezolid by HPLC.

Saturation solubility of linezolid in pure water at pH 7 was determined separately to be 2.9±0.1 mg/ml. Saturation solubility of linezolid in aqueous SB-β-CD solutions was determined as shown in Table 1.

TABLE 1

Saturation solubility of linezolid in SB-β-CD solutions

| SB-β-CD concentration (mg/ml) | Solubility of linezolid (mg/ml) |
|---|---|
| 10 | 4.3 |
| 50 | 9.5 |
| 100 | 15.9 |
| 150 | 22.1 |
| 250 | 33.4 |
| 500 | 59.9 |

Example 2

A buffered isotonic solution was prepared at pH 4.5, 283 mOsm/kg using a 10 mM citrate buffer solution (0.851 mg/ml citric acid, 1.638 mg/ml sodium citrate) containing 23 mg/ml dextrose and 50 mg/ml SB-β-CD. To 20 ml of this solution was added 100 mg linezolid with heating and stirring until the linezolid was completely dissolved. The resulting solution contained approximately 5 mg/ml linezolid.

Example 3

A buffered isotonic solution was prepared at pH 4.5, 285 mOsm/kg using a 10 mM citrate buffer solution (0.851 mg/ml citric acid, 1.638 mg/ml sodium citrate) containing 100 mg/ml SB-β-CD. To 20 ml of this solution was added 200 mg linezolid with heating and stirring until the linezolid was completely dissolved. The resulting solution contained approximately 10 mg/ml linezolid.

Example 4

A buffered isotonic solution was prepared at pH 4.5, 289 mOsm/kg using a 10 mM citrate buffer solution (0.851 mg/ml citric acid, 1.638 mg/ml sodium citrate) containing 100 mg/ml SB-β-CD. To 100 ml of this solution was added 800 mg linezolid with heating to about 60° C. and stirring until the linezolid was completely dissolved. The resulting solution contained approximately 8 mg/ml linezolid.

The solution was filtered using 0.2 μm Nalgene filterware, and 10 ml of filtered solution was filled into each of ten Kimble-Warsaw Type I glass bottles stoppered with Daikyo 777 stoppers. Eight of the bottles were placed in a 25° C. constant temperature cabinet and two of the bottles were placed in a laboratory refrigerator at 4–6° C.

No precipitation or color changes were evident after storage for two months under these conditions.

Example 5

A study was conducted to examine solubility of three oxazolidinone compounds, herein denoted Compound 1, Compound 2 and Compound 3, in an aqueous system containing hydroxypropyl-β-cyclodextrin ("HP-β-CD").

Compound 1 is (S)-N-[[3-[3-fluoro-4-(4-(hydroxyacetyl)-1-piperazinyl)phenyl]-2-oxo-5-oxazolidinyl]methyl] acetamide.

Compound 2 is (S)-N-[[3-[3-fluoro-4-(4-morpholinyl)phenyl]-2-oxo-5-oxazolidinyl]methyl]acetamide (linezolid).

Compound 3 is (S)-N-[[3-[3-fluoro-4-(1,1-dioxothiomorpholin-4-yl)phenyl]-2-oxo-5-oxazolidinyl]methyl]acetamide.

Aqueous solutions of HP-β-CD at concentrations of 0, 60, 100, 200, 300 and 400 mg/ml were prepared. Compound 1, 2 or 3 in excess amount was added to each solution. The solutions were stirred for 48 h at 37° C. and were then filtered and assayed by HPLC to provide a measure of saturation solubility of Compounds 1, 2 and 3 in each HP-β-CD solution.

The saturation solubilities observed in this Example are shown in graphical form in FIG. 1. Saturation solubility of each oxazolidinone compound was found to be linearly related to HP-β-CD concentration.

Example 6

An aqueous Linezolid Suspension Formulation was prepared, having the following composition:

| | |
|---|---|
| Linezolid | 5% |
| Sodium Citrate | 4% |
| Soya Lecithin | 1% |
| Poly Vinyl Pyrrolidone | 0.1% |

A preservative free aqueous Linezolid Solution Formulation was also prepared, having the following composition:

| | |
|---|---|
| Linezolid | 5% |
| Hydroxypropyl-β-cyclodextrin | 25% |

Both of the above two formulations, containing 50 mg/ml of linezolid in an aqueous medium, were administered to rabbit eyes to assess the concentration of linezolid in the lacrimal fluid, cornea and conjunctiva, 1 hour after application. In 1 ml of the formulation 0.5 mg of linezolid was $^{14}$C-labeled and 50 mg was unlabeled.

Four healthy male New Zealand white rabbits of body weight 1.8 to 2.5 kg were assigned to treatment with the formulation. To each of the eyes of the rabbit, 25 μl of the test formulation was applied using a pipette. Rabbits were sacrificed 1 hour after application, and eye tissues were excised. Just prior to sacrifice, lacrimal fluid was collected from each eye (Linezolid Solution Formulation, only). Lacrimal fluid and excised tissues were combusted for liquid scintillation counting to determine radioactivity as a measure of amount of radioactivity present (Linezolid Solution Formulation, only). Radioactive counts were converted by calculation to concentration of linezolid in μg/g. The results are presented below.

| Linezolid concentration (μg/g) in | Suspension Formulation | Solution Formulation |
|---|---|---|
| Lacrimal Fluid | NA | 505 |
| Conjunctiva | 8.3 | 18.7 |
| Cornea | NA | 11.2 |
| Aqueous Humor | NA | 2.7 |

It is seen from the above table that high levels of linezolid were achieved in the ocular tissues with the solubilized formulation (i.e., the Linezolid Solution Formulation), even though the suspension (i.e. Linezolid Suspension Formulation) was specifically designed to be retained longer in the eye.

The results above are likely due, at least in part, to the fact that the Linezolid Solution Formulation tested in this case contained a higher concentration of dissolved linezolid than the Linezolid Suspension Formulation. Also, the Linezolid Solution Formulation did not contain any preservatives likely to inhibit solubilization of linezolid by the cyclodextrin component of the formulation (i.e., hydroxypropyl-β-cyclodextrin).

What is claimed is:

1. A pharmaceutical composition suitable for topical administration to an eye, comprising:
   (a) an oxazolidinone antibiotic drug in a concentration effective for treatment and/or prophylaxis of a gram-positive bacterial infection of at least one tissue of the eye, the concentration being above the practical limit of solubility of the drug in an aqueous solution at a physiologically compatible pH; and
   (b) a pharmaceutically acceptable cyclodextrin compound in a cyclodextrin concentration sufficient to maintain the drug in solution at the drug concentration,
   wherein, the pharmaceutical composition is preservative free.

2. The composition of claim 1 wherein the oxazolidinone antibiotic drug is a compound of formula

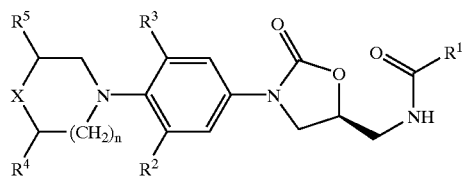

wherein:
   $R^1$ is selected from (a) H, (b) $C_{1-8}$ alkyl optionally substituted with at least one F, Cl, OH, $C_{1-8}$ alkoxy, and $C_{1-8}$ acyloxy or $C_{1-8}$ benzoxy, including a $C_{3-6}$ cycloalkyl group, (c) amino, (d) mono- and di($C_{1-8}$ alkyl)amino and (e) $C_{1-8}$ alkoxy groups;
   $R^2$ and $R^3$ are independently selected from H, F and Cl groups;
   $R^4$ is H or $CH_3$;
   $R^5$ is selected from H, $CH_3$, CN, $CO_2R^1$ and $(CH_2)_m R^6$ groups, where $R^1$ is as defined above, $R^6$ is selected from H, OH, $OR^1$, $OCOR^1$, $NHCOR^1$, amino, mono- and di($C_{1-8}$ alkyl)amino groups, and m is 1 or 2;
   n is 0, 1 or 2; and
   X is O, S, SO, $SO_2$, $SNR^7$ or $S(O)NR^7$ where $R^7$ is selected from H, $C_{1-4}$ alkyl (optionally substituted with one or more F, Cl, OH, $C_{1-8}$ alkoxy, amino, $C_{1-8}$ mono- or di($C_{1-8}$ alkyl)amino groups), and p-toluenesulfonyl groups;
   or a pharmaceutically acceptable salt thereof.

3. The composition of claim 2 wherein, in said formula, $R^1$ is $CH_3$; $R^2$ and $R^3$ are independently selected from H and F but at least one of $R^2$ and $R^3$ is F; $R^4$ and $R^5$ are each H; n is 1; and X is selected from O, S and $SO_2$.

4. The composition of claim 1 wherein the oxazolidinone antibiotic drug is selected from the group consisting of: linezolid, eperezolid, N-((5S)-3-(3-fluoro-4-(4-(2-fluoroethyl)-3-oxopiperazin-1-yl)phenyl)-2-oxooxazolidin-5-ylmethyl)acetamide, (S)-N-[[3-[5-(3-pyridyl)thiophen-2-yl]-2-oxo-5-oxazolidinyl]methyl]acetamide, (S)-N-[[3-[5-(4-pyridyl)pyrid-2-yl]-2-oxo-5-oxazolidinyl]methyl]acetamide hydrochloride and N-[[(5S)-3-[4-(1,1-dioxido-4-thiomorpholinyl)-3,5-difluorophenyl]-2-oxo-5-oxazolidinyl]methyl]acetamide.

5. The composition of claim 1 wherein the oxazolidinone antibiotic drug is linezolid.

6. The composition of claim 1, wherein the oxazolidinone drug concentration is about 0.1 mg/ml to about 100 mg/ml.

7. The composition of claim 1 wherein the cyclodextrin compound is selected from the group consisting of α-cyclodextrin, β-cyclodextrin, γ-cyclodextrin, an alkylcyclodextrin, a hydroxyalkylcyclodextrin, a carboxyalkylcyclodextrin, and sulfoalkylether cyclodextrin.

8. The composition of claim 1 wherein the cyclodextrin compound is selected from the group consisting of hydroxypropyl-β-cyclodextrin and sulfobutylether-β-cyclodextrin.

9. The composition of claim 1 wherein the cyclodextrin compound is present at a concentration of about 1 to about 500 mg/ml.

10. The composition of claim 1, further comprising at least one ophthalmically acceptable excipient that reduces a rate of removal of the composition from the eye by lacrimation, such that the composition has an effective residence time in the eye of about 2 to about 24 hours.

11. The composition of claim 1, further comprising an in situ gellable material in a form selected from a solution, a suspension and a solution/suspension, wherein the in situ gellable material has an ophthalmically compatible pH and osmolality.

12. The composition of claim 1, further comprising a buffering agent and/or an agent for adjusting osmolality in amounts whereby the solution is substantially isotonic and has an ophthalmically acceptable pH.

13. A method of treating an eye infection in a subject, comprising administering to the subject a therapeutically effective dose of a pharmaceutical composition suitable for topical administration to an eye, comprising:

an oxazolidinone antibiotic drug in a drug concentration effective for treatment and/or prophylaxis of a gram-positive bacterial infection of at least one tissue of the eye, the drug concentration being above the practical limit of solubility of the drug in a substantially isotonic aqueous solution at a physiologically compatible pH; and a pharmaceutically acceptable cyclodextrin compound in a cyclodextrin concentration sufficient to maintain the drug in solution at the drug concentration, wherein, the pharmaceutical composition is preservative free.

14. The method of claim 13, wherein the subject is a mammal.

15. The method of claim 13, wherein the subject is a human being.

16. The method of claim 13 wherein the oxazolidinone antibacterial drug is a compound of formula

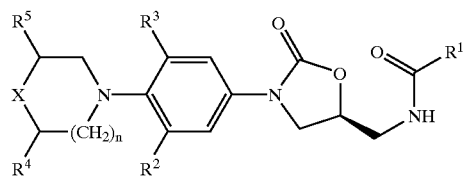

wherein:

$R^1$ is selected from (a) H, (b) $C_{1-8}$ alkyl optionally substituted with at least one F, Cl, OH, $C_{1-8}$ alkoxy, and $C_{1-8}$ acyloxy or $C_{1-8}$ benzoxy, including a $C_{3-6}$ cycloalkyl group, (c) amino, (d) mono- and di($C_{1-8}$ alkyl)amino and (e) $C_{1-8}$ alkoxy groups;

$R^2$ and $R^3$ are independently selected from H, F and Cl groups;

$R^4$ is H or $CH_3$;

$R^5$ is selected from H, $CH_3$, CN, $CO_2R^1$ and $(CH_2)_mR^6$ groups, where $R^1$ is as defined above, $R^6$ is selected from H, OH, $OR^1$, $OCOR^1$, $NHCOR^1$, amino, mono- and di($C_{1-8}$ alkyl)amino groups, and m is 1 or 2;

n is 0, 1 or 2; and

X is O, S, SO, $SO_2$, $SNR^7$ or $S(O)NR^7$ where $R^7$ is selected from H, $C_{1-4}$ alkyl (optionally substituted with one or more F, Cl, OH, $C_{1-8}$ alkoxy, amino, $C_{1-8}$ mono- or di($C_{1-8}$ alkyl)amino groups), and p-toluenesulfonyl groups;

or a pharmaceutically acceptable salt thereof.

17. The method of claim 16 wherein, in said formula, $R^1$ is $CH_3$; $R^2$ and $R^3$ are independently selected from H and F but at least one of $R^2$ and $R^3$ is F; $R^4$ and $R^5$ are each H; n is 1; and X is selected from O, S and $SO_2$.

18. The method of claim 13 wherein the oxazolidinone antibacterial drug is selected from the group consisting of: linezolid, eperezolid, N-((5S)-3-(3-fluoro-4-(4-(2-fluoroethyl)-3-oxopiperazin-1-yl)phenyl)-2-oxooxazolidin-5-ylmethyl)acetamide, (S)-N-[[3-[5-(3-pyridyl)thiophen-2-yl]-2-oxo-5-oxazolidinyl]methyl]acetamide, (S)-N-[[3-[5-(4-pyridyl)pyrid-2-yl]-2-oxo-5-oxazolidinyl]methyl]acetamide hydrochloride and N-[[(5S)-3-[4-(1,1-dioxido-4-thiomorpholinyl)-3,5-difluorophenyl]-2-oxo-5-oxazolidinyl]methyl]acetamide.

19. The method of claim 13 wherein the oxazolidinone antimicrobial drug is linezolid.

20. The method of claim 19, wherein the ophthalmic formulation is administered in a dose of about 1 to about 100 mg of linezolid at least once per day.

21. A pharmaceutical composition suitable for topical administration to an eye, comprising:

(a) linezolid in a concentration effective for treatment and/or prophylaxis of a gram-positive bacterial infection of at least one tissue of the eye, the concentration being above the practical limit of solubility of linezolid in an aqueous solution at a physiologically compatible pH; and (b) a pharmaceutically acceptable cyclodextrin compound in a cyclodextrin concentration sufficient to maintain the drug in solution at the drug concentration, wherein, the pharmaceutical composition is preservative free.

22. The composition of claim 21, wherein the linezolid concentration is about 0.1 mg/ml to about 100 mg/ml.

23. The composition of claim 21 wherein the cyclodextrin compound is selected from the group consisting of α-cyclodextrin, β-cyclodextrin, γ-cyclodextrin, an alkylcyclodextrin , a hydroxyalkylcyclodextrin, a carboxyalkylcyclodextrin, and sulfoalkylether cyclodextrin.

24. The composition of claim 21 wherein the cyclodextrin compound is selected from the group consisting of hydroxypropyl-β-cyclodextrin and sulfobutylether-β-cyclodextrin.

25. The composition of claim 21 wherein the cyclodextrin compound is present at a concentration of about 1 to about 500 mg/ml.

* * * * *